United States Patent [19]
Dietz et al.

[11] Patent Number: 5,989,918
[45] Date of Patent: Nov. 23, 1999

[54] ADME ANALYSIS OF MIXTURES

[75] Inventors: Corine M. Dietz, San Francisco; Jacqueline A. Gibbons; Eric W. Taylor, both of Oakland, all of Calif.

[73] Assignee: Chiron Corporation, Emeryville, Calif.

[21] Appl. No.: 08/919,921

[22] Filed: Aug. 28, 1997

Related U.S. Application Data

[60] Provisional application No. 60/024,518, Aug. 29, 1996.

[51] Int. Cl.$^6$ .......................... G01N 33/48; A01N 29/00
[52] U.S. Cl. .......................... 436/63; 436/124; 436/503; 435/1.1; 435/1.2; 514/832; 514/743; 514/746; 514/744; 514/759; 604/4
[58] Field of Search ........................ 436/124, 63, 503; 604/4; 422/44; 435/1.1, 1.2; 514/832, 746, 759, 744, 743

[56] References Cited

U.S. PATENT DOCUMENTS 4,666,425  5/1987  Fleming ...................................... 604/4

OTHER PUBLICATIONS

Pellegrin et al., European Journal of Drug Metabolism and Pharmacokinetics., 1985., vol. 10., No. 2., pp. 113–120.
Takahashi et al., "The Use of a Perfluorochemical Emulsion as a Vascular Perfusate in Drug Absorption" *J. Pharm. Pharmacol.* 40:252–257, 1988.
Geyer, "'Bloodless' Rats Through the Use of Artificial Blood Substitutes" *Federation Proceedings* 34(6):1499–1505, May, 1975.
Baba et al., "Ex–Vivo Perfusion of Surgically Removed Organs" *Biomat. Art. Cells Art. Org.* 16(1–3): 623–624, 1988.
Faithfull, "Fluorocarbons Current Status and Future Applications" *Anaesthesia* 42:234–242, 1987.
Dietz et al., "ADME Characterization of Complex Chemical Mixtures in vivo: Development of a Method to Analyze Mixtures of 24 Molecules in an Oxygen–Carrying Blood Substitute" *Pharmaceutical Research* 13(9 Suppl), 1996, Abstract No. PPDM 8426.
Spence, "Perfluorocarbons in the Twenty–First Century: Clinical Applications as Transfusion Alternatives" *Art. Cells, Blood Subs., and Immob. Biotech.* 23(3):367–380, 1995.
Spence, "Perfluorocarbons as Blood Substitutes: the Early Years Experience with Fluosol DA–20% in the 1980s" *Art. Cells, Blood Subs., and Immob. Biotech.* 22(4):955–963, 1994.
Noble, "Artificial Blood" *Analytical Chemistry* 67(1):31A–33A, Jan., 1995.
Flaim, "Pharmacokinetics and Side Effects of Perfluorocarbon–Based Blood Substitutes" *Art. Cells, Blood Subs., and Immob. Biotech.* 22(4):1043–1054, 1994.
Marchbank, "Fluorocarbon Emulsions" *Perfusion* 10:67–88, 1995.
Luo et al., Poster Presented at the 14th Symposium on Liquid Chromatography/Mass Spectrometry (L.C./MS, CF/MS, MS/MS) at Cornell University, Ithaca, New York, Jul. 23–25, 1997, poster entitled "Development of a Quantitative Method for Measuring Chemical Mixtures in a Perfluorocarbon Based Oxygen–Carrying Blood Substitute Using LC/MS".

*Primary Examiner*—Keith D. MacMillan
*Assistant Examiner*—P. Ponnaluri
*Attorney, Agent, or Firm*—Merchant Gould Smith Edell Welter & Schmidt; Sharon M. Fujita; Robert P. Blackburn

[57] ABSTRACT

A method for analyzing the ADME/PK properties of a mixture of compounds is (1) perfusing an animal or organ with a perfluorocarbon emulsion blood substitute, (2) administering the mixture of test compounds, (3) withdrawing an aliquot of the perfusate, (4) disrupting the emulsion, and (5) analyzing the aqueous phase of the perfusate for the concentration of test compounds.

6 Claims, 2 Drawing Sheets

ADME ANALYSIS OF MIXTURES

CROSS-REFERENCE TO RELATED APPLICATION

This application claims the benefit of U.S. Provisional Application Ser. No. 60/024,518, filed Aug. 29, 1996.

FIELD OF THE INVENTION

This invention relates to the fields of pharmacokinetics and pharmacological research. More specifically, the invention describes the concept of using perfluorocarbon emulsions for examining the ADME/PK (absorption, distribution, metabolism, excretion and pharmacokinetics) properties of chemical mixtures in animals and a method for preparing the emulsions for direct analysis by techniques such as high performance liquid chromatography (HPLC), mass spectrometry and capillary electrophoresis.

BACKGROUND OF THE INVENTION

Drug development begins with the identification of a lead compound, based on the ability of the compound to exhibit a desired biological effect, such as the ability to inhibit bacterial growth, inhibit the activity of a target enzyme, increase or modulate the uptake of neurotransmitters, and the like. Biological activity is typically determined on the basis of in vitro experimentation or assays designed to rapidly identify candidate drugs. Typically, only a small percentage of the compounds tested will demonstrate sufficient activity and selectivity to merit further investigation.

Once a candidate or lead compound has been identified and selected for further development, its ADME/PK characteristics are determined. ADME/PK concerns the absorption, distribution, metabolism, excretion and pharmacokinetics of drugs in the body. The ADME/PK properties of a drug are critical, and often serve to distinguish pharmaceutical products from mere lead compounds. For example, a drug that is poorly absorbed orally may require intravenous (or other parenteral) administration to be effective, which may be unacceptable for the condition to be treated. A compound effective as an antibiotic may be ineffective to treat bacterial meningitis if its distribution does not carry it to the central nervous system. A compound that is rapidly metabolized and/or excreted may not reside in the body long enough to serve its intended purpose. These properties are all independent of the drug candidate's in vitro activity, and are difficult or impossible to predict based on current information. The complex factors that influence ADME/PK make it hard to model accurately, and necessitate the use of living tissues and research animals before a compound may proceed with clinical trials.

To enhance the speed of drug discovery and reduce the number of animals required, it is desirable to characterize the ADME/PK of mixtures of lead compounds (rather than single compounds) in procedures that involve either living animals (i.e., in vivo), or isolated organs or organ systems from animals.

In in vivo analyses of ADME/PK, plasma is generally the biophase used as the analytical endpoint. Measurement of individual drug candidates in plasma typically involves a unique extraction method based on the physicochemical properties of each molecule, in order to separate and quantify the compound from the numerous plasma components. Optimization of one plasma extraction method for all components of a chemical mixture poses a major problem for rapid screening.

SUMMARY OF THE INVENTION

We have now invented a method for improving the ADME/PK analysis of candidate compounds, by replacing the blood of a test animal or tissue with an emulsified blood substitute, administering a test compound, and analyzing the resulting blood substitute. Preferably, the test compound is administered as a mixture of test compounds.

Another aspect of the invention is the method for designing libraries of pharmaceutical candidates based on ADME/PK properties.

DETAILED DESCRIPTION

Definitions

Figure 1:
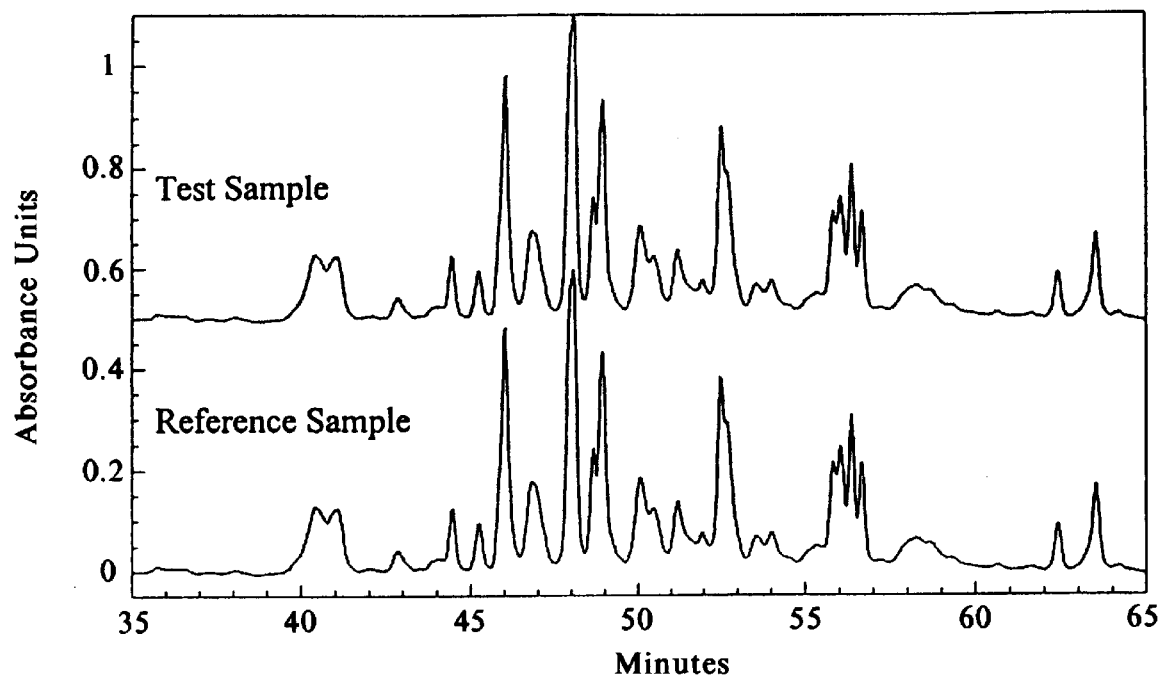
FIG. 1 shows the uv RP-HPLC trace obtained from a mixture of compounds added to a perfluorocarbon emulsion before ("test sample") or after ("reference sample") the emulsion is disrupted.

The term "ADME/PK" refers to the absorption, distribution, metabolism, and excretion pharmacokinetics of a pharmaceutical compound or potential pharmaceutical compound, upon administration to an animal, isolated organ, or a tissue. "Animal" includes all animals useful in pharmaceutical research, preferably warm-blooded animals, more preferably mammals, up to and including humans.

The term "blood substitute" refers to a fluid which may be used to replace the blood of a test animal, or may be used to perfuse an isolated organ in the absence of blood, and is sufficient to sustain the life of the animal, organ or tissue for the duration of the experiment. Preferred blood substitutes for the purposes of this invention are those which contain few or no components that are chemically similar to the pharmaceutical candidates under evaluation. Presently preferred blood substitutes are fluorocarbon emulsions, such as those described by Geyer, *Fed Proc* (1975) 34:1499–1505; Geyer, "Advances in Blood Substitute Research" (Alan R. Liss, Inc., NY, N.Y., 1983), pp. 157–68; Spence, *Art. Cells Blood Subs., and Immob. Biotech.* (1994) 22(4):955–963; Spence, *Art. Cells, Blood Subs., and Immob. Biotech.* (1995) 23(3): 367–380; and Dracker, *Immunol Invest* (1995) 24:403–10, all of which are incorporated herein by reference.

The term "perfluorocarbon" as used herein refers to an organic molecule in which all hydrogens bound to carbon atoms have been replaced with fluorine atoms. Thus, for example, perfluoroethane has the formula $F_3C$—$CF_3$. As a group, they are characterized by insolubility in aqueous solutions, low viscosity and a specific gravity approximately twice that of water. Liquid perfluorocarbons dissolve considerable quantities of oxygen and carbon dioxide (and other non-polar gasses) in simple solution, the dissolved concentration in direct proportion to the partial pressure according to Henry's Law. Perfluorocarbon compounds are generally heat-stable and are biochemically inert due to the high carbon-fluorine bond energy. The hydrophobic nature of the fluoride renders it impervious to enzymatic attack. Perfluorocarbons are used in vivo by emulsifying the compounds into small particles (typically 0.1–0.3 microns in diameter) by sonication in the presence of a detergent or surfactant. Perfluorocarbons are suitable for the practice of the instant invention if they make acceptable blood substitutes. Exemplary perfluorocarbons include, without limitation, perfluorotributylamine, perfluorodecalin, perfluorooctyl bromide, perfluorotripropyl-amine, bis(perfluorobutyl) ethylene, perfluoro-N,N-dimethylcyclohexylmethylamine, perfluorotrimethylbicyclo(3.3.1)nonane, perfluorobicyclo (5.3.0)decane, and perfluorobutyltetrahydrofuran.

The term "surfactant" refers to a "surface-active" agent, in the present case, one useful for emulsifying perfluorocarbon compounds in an aqueous suspension. Preferred surfactants will be generally non-toxic (for the duration of the experiments contemplated). Suitable surfactants include, without limitation, lecithin-based surfactants, egg yolk phospholipids, and synthetic surfactants such as poloxamers (available commercially as Pluronic® polyols). Poloxamers are polyoxyethylene-polyoxypropylene block polymers, which are available in a wide range of molecular weights and HLB (hydrophilic/lipophilic balance) values. The currently preferred poloxamer is poloxamer-188 (also known as Pluronic F68). See, for example, Hammerschmidt et al., "Blood Substitutes" (T. M. S. Chang, ed., Marcel Dekker, Inc., NY 1988) pp. 431–38; Breuninger et al., *J. Pediatr Surg* (1993) 28:144–50; Mattrey et al., *Crit Care Med* (1989) 17:652–56, all of which are incorporated herein by reference.

The term "water-miscible organic solvent" refers to an organic solvent which may be mixed with aqueous solutions, and which disrupt (or break) perfluorocarbon emulsions. Suitable water-miscible organic solvents include alcohols such as propanol, isopropanol, butanol, cyclohexanol, and the like; amines such as triethylamine; and other solvents such as acetonitrile, tetrahydrofuran, pyridine, and the like. Presently preferred water-miscible organic solvents are isopropanol and acetonitrile.

The term "isolated organ" refers to a living organ or organ system, such as a kidney, lung, gastrointestinal tract, heart, liver, brain, and the like, with the accompanying vasculature. In general, isolated organs will be selected for their utility in demonstrating or suggesting ADME/PK properties for pharmaceutical compounds (or potential pharmaceutical compounds).

General Methods and Detailed Description

By replacing blood in rats with a perfluorocarbon-containing blood substitute, the quantitation of diverse chemical mixtures can be accomplished by an assortment of analytical methods without extraction steps specific to each component of a mixture.

In ADME/PK procedures involving isolated organs and organ systems, the organs are typically oxygenated by perfusion with either blood or an aqueous buffer. Viability of the organs is generally good with blood as the perfusate, but, as noted above, this medium is not readily amenable to facile quantitation of the components of chemical mixtures. In contrast, aqueous buffers have the potential for simple analysis of mixture components, but may result in loss of tissue viability due to the poor capacity of such media to transport oxygen. Thus, the use of perfluorocarbon-containing blood substitutes in isolated organs or organ systems holds two key benefits: 1) facile measurement of multiple analytes in the perfusate; and 2) enhanced tissue viability relative to that achieved with aqueous buffers.

The invention provides for characterization of ADME/PK of chemical mixtures in experiments with either living animals or isolated organs or organ systems from animals. Two processes are included, one involving the use of perfluorocarbon emulsions to examine chemical mixtures in animals, and one involving the preparation of perfluorocarbon emulsions for assay by standard analytical methods. The process of the invention involving animals entails the replacement of blood in the blood vasculature with a perfluorocarbon emulsion, followed by administration of a chemical mixture to the test animal or isolated organ or organ system. The ADME/PK fate of the mixture components is then followed over time in the perfluorocarbon emulsion using a new analytical procedure. In the analytical procedure, there is an initial chemical disruption of the emulsion by addition of a water-miscible organic solvent (such as isopropanol), followed by centrifugation to separate the medium into discrete phases. The supernatant phase is then analyzed directly by any of a number of methods, including HPLC, mass spectrometry and capillary electrophoresis.

A variety of blood substitutes are taught in the literature and/or are commercially available. An appropriate blood substitute for the present invention is selected to (1) provide sufficient oxygen to the animal or tissues under investigation for at least the duration of the experiment, and (2) contribute the least number of interfering substances, i.e., compounds which might interact with the compounds being tested, or which might be confused with the compounds being tested under the experimental conditions.

Presently preferred blood substitutes are perfluorocarbon emulsions. Perfluorocarbon emulsions employed in the practice of the present invention typically contain at least about 5% (w/v) of a perfluorocarbon, more typically at least about 10% (w/v), even more typically at least about 12% (w/v), yet even more typically at least about 15% (w/v), and optionally, they contain at least about 20% (w/v) of a perfluorocarbon. Suitable perfluorocarbon emulsions typically contain less than about 90% (w/v) of a perfluorocarbon, more typically less than about 85% (w/v), even more typically less than about 80% (w/v), yet even more typically less than about 75% (w/v), more typically less than about 70% (w/v), and optionally, they contain less than about 65% (w/v) of a perfluorocarbon. Preferably, perfluorocarbon emulsions of the present invention contain at least about 20% (w/v) of a perfluorocarbon.

The experimental design will, of course, depend upon the compounds being tested, the intended route of administration, and the particular ADME/PK characteristics to be determined. For example, one may study the absorption of test compounds from the gut by perfusing an animal or an isolated portion of gastrointestinal tract, administering the compound or mixture of compounds, and monitoring the rate of appearance of the compound(s) in the perfusate. Similarly, one might study the rate of removal from the system by adding the compound(s) directly to the perfusion fluid, and measuring the rate at which the compounds disappear from the perfusate. First-pass metabolism may be studied through perfusion experiments employing the liver.

This information can then be used to screen compounds (or whole libraries of compounds) for potential bioavailability, permitting one to research compounds that have the best chance of being useful as biopharmaceutical agents. For example, one might find that all triazine compounds in a diverse library were metabolized rapidly by the liver. This information may lead one to forego the examination of triazine libraries in future applications in which first pass metabolism is possible. Alternatively, one might find that compounds having a particular moiety were rapidly absorbed, which may lead one to design libraries of compounds which all employ that moiety. Conversely, one might find that all compounds from a library that included a large hydrophobic group were not orally absorbed, leading one to design compound libraries that eschew that feature when designing compounds for oral administration. Thus, one may employ the data generated to select particular libraries for particular applications, and may in fact design libraries to incorporate chemical features that provide the desired ADME/PK characteristics. In this method, a target property is identified (for example, transmission across the blood-brain barrier), and the ADME/PK characteristics of a mixture of compounds having diverse structural and chemical properties is determined. The data resulting from the ADME/PK determination are analyzed for structural and chemical features that maximize transmission across the blood-brain barrier, and that information is then used to design a library of compounds which incorporate the appropriate features.

Mixtures of compounds may be prepared by any of a variety of methods, for example by the techniques taught in WO91/09735 and WO94/0645 1, both incorporated herein by reference, or by simply mixing compounds together. The techniques of the invention are useful for analysis of both compound mixtures and single compounds, as the invention provides a biophase essentially free of contaminating proteins (apart from 1–2 well-defined peaks), and a universal extraction procedure.

In the method of the invention, the perfusate is preferably analyzed by disrupting the emulsion, separating the aqueous and non-aqueous phases, and analyzing the aqueous phase (e.g., by reverse-phase HPLC, thin layer chromatography, and the like). Perfluorocarbon emulsions may typically be disrupted by adding a water-miscible organic solvent such as isopropanol or acetonitrile, optionally in the presence of a saline solution. Once disrupted, the two phases of the emulsion may be allowed to separate on standing, but are preferably separated by centrifugation. Other solvents and methods for disrupting emulsions may be employed, if desired. In general, the analysis method will be advantageous if it (1) partitions the compounds under investigation into the aqueous phase, and (2) preferably causes precipitation of any plasma proteins in the non-aqueous phase.

One may also deliberately incorporate a plasma protein to study the interaction between the test compounds and the protein, for example to examine binding to serum albumin and its effect on the plasma half-life of the test compounds.

The examples presented below are provided as a further guide to the practitioner of ordinary skill in the art, and are not to be construed as limiting the invention in any way.

EXAMPLE 1

Demonstration of Compound Partition

Perfluorocarbon emulsions are prepared for analysis by initially disrupting the emulsion with a water-miscible organic solvent (such as isopropanol), followed by centrifugation to separate the medium into discrete phases. The supernate is then directly analyzed by any of a number of methods, including HPLC, mass spectrometry and capillary electrophoresis. Since only the supernatant fraction is subject to analysis, analytes sequestered in the pelleted fraction would not be detected in measurements. Analysis of the supernate would thus fail to provide a method for universally determining the concentrations of analytes in perfluorocarbon emulsions. We therefore addressed the question of whether the supernate derived from a perfluorocarbon emulsion provides an unbiased view of the analytes present in the emulsion.

Preparation of Test Samples. Three chemical mixtures were used: CHIR 4565, CHIR 4575, and CHIR 4582 (Chiron Corp., Emeryville, Calif.), each containing 24 oligo-N-substituted glycines (see WO91/09735 and WO94/0645 1, both incorporated herein by reference). A stock solution was prepared for each of the mixtures with the components of the mixtures equimolar at 0.2 mM in DMSO. Test samples were prepared for each of the mixtures as follows. In a 1.5-ml microfuge tube, a 10-$\mu$l aliquot of the stock solution was dissolved in 0.250 ml of a perfluorotributylamine-based emulsion sold under the product name OXYPHEROL-ET EMULSION™ (Alpha® Therapeutic Corp., Los Angeles, Calif.) and stirred on a vortex mixer for 30 sec. To chemically disrupt the emulsion, 0.30 ml of isopropyl alcohol (Fisher Scientific, Fair Lawn, N.J.) and 50 $\mu$l of 35% sodium chloride were each added to the sample. The solution was stirred on a vortex mixer for 1 min and the perfluorocarbon sedimented by centrifugation at 16,000×G for 8 min. A 0.50-ml portion of the supernate (83% of the total volume of supernate) was removed for further analysis.

Preparation of Reference Samples. A 0.250-ml portion of OXYPHEROL-ET EMULSION™ was phase-separated as described above for the preparation of the test samples. For the reference samples, however, the chemical mixtures were added in the final, rather than the initial procedure. Thus, 8.3 $\mu$l of a chemical mixture was added to a 0.50-ml portion of supernate. (It should be noted that while 10 $\mu$l of stock solution was added to the test samples, only 83% of the total volume of supernate was retrieved for further analysis; thus 83% of 10 $\mu$l, or 8.3 $\mu$l of stock solution was added to the reference samples.)

Preparation of Blank Samples. A 25-$\mu$l aliquot of DMSO was dissolved in 0.250 ml of OXYPHEROL-ET EMULSION™. This solution was subject to phase-separation as described above for the preparation of the test samples.

Preparation of the Samples for HPLC analysis. The test, reference and blank samples were lyophilized in a vacuum concentrator equipped with a refrigerated condenser trap (Savant Instruments, Inc., Hicksville, N.Y.). A 0.1 ml volume of medium containing 2% acetonitrile, 0.2% heptanesulfonic acid, and 0.1% trifluroacetic acid in water (pH 2) was added to each sample, and the lyophilized material was dissolved by stirring the solution on a vortex mixer for approximately 3 min. For calibration of sample recovery on the HPLC system, lucifer yellow (Molecular Probes, Eugene, Oreg.) was added to each sample at 10 ng/ml. A 25-$\mu$l volume of sample was added to 75 $\mu$l of HPLC buffer A (described below) prior to injection onto the HPLC system.

Reverse-Phase High Performance Liquid Chromatography. Analysis of the samples was performed by reverse-phase HPLC using a $C_{18}$ Monitor column (5 $\mu$×150 mm, 100 Å pore size; Michrom BioResources Inc., Auburn, Calif.). The column was attached to a microbore HPLC system (Michrom BioResources, Inc.). The mobile phases for the chromatography were: HPLC buffer A, (2% acetonitrile, 0.2% heptanesulfonic acid, and 0.2% trifluroacetic acid in water, pH 3); and HPLC buffer B (75% acetonitrile, 0.2% heptanesulfonic acid, and 0.08% trifluroacetic acid in water, pH 2). The flow rate was maintained at 50 $\mu$l/min and a linear gradient was implemented with a 37 min transition from 0 to 100% buffer B. The eluent was monitored with two detectors: 1) a uv detector set at 215 nm (for monitoring the components of the chemical mixtures); and 2) a fluorometric detector with excitation and emission set at 425 and 530 nm, respectively (for monitoring the lucifer yellow).

Summary of Results. To evaluate recovery of the components of the mixtures, HPLC "handprints" (i.e., the shapes of the chromatograms) were compared for the test and reference samples. The plot shown in FIG. 1 is typical of the HPLC handprints that were obtained in the experiment. The good correlation between the two HPLC chromatograms in the plot qualitatively demonstrates that the supernate derived from a perfluorocarbon emulsion successfully provides an unbiased measure of the components of CHIR 4565 in the emulsion.

To quantitatively assess recovery of the mixture components, the peak areas were integrated and summed, and the recoveries calculated by comparing the areas for the test and reference samples. This was repeated 2 to 3 times for each mixture; the table below reports the means and standard deviations of these multiple trials.

| Chemical Mixture | Chemical Properties | Recovery of Components* |
|---|---|---|
| CHIR-4582 | Moderately hydrophobic | 87 ± 5% |
| CHIR-4575 | Hydrophilic, basic | 82 ± 1% |
| CHIR-4565 | Hydrophilic, zwitterionic | 92 ± 5% |

*ANOVA comparing the mixtures, p-value: 0.1772

Overall, the results presented in this example confirm that our method of chemical disruption followed by centrifugation provides a facile and reliable method for analyzing complex chemical mixtures in a perfluorocarbon emulsion.

EXAMPLE 2

Emulsion Disruption with Protein Precipitation (A) Disruption with acetonitrile: Since perfluorocarbon emulsions are prepared free of proteins, replacement of blood with an emulsion will result in a gradual diffusion of proteins from the tissues to the emulsion (Geyer, supra). In terms of the analysis, this could potentially be problematic, since proteins are generally incompatible with measurements of analytes by conventional methods such as HPLC. Acetonitrile was considered an attractive agent for eliminating proteins from perfluorocarbon emulsions, since it is well known to cause efficient precipitation of plasma proteins.

In this set of experiments we set out to determine: (1) whether acetonitrile can be used in place of isopropanol to chemically disrupt perfluorocarbon emulsions; and (2) whether disruption of the emulsion using acetonitrile eliminates bulk plasma proteins from the supernate.

Figure 2:
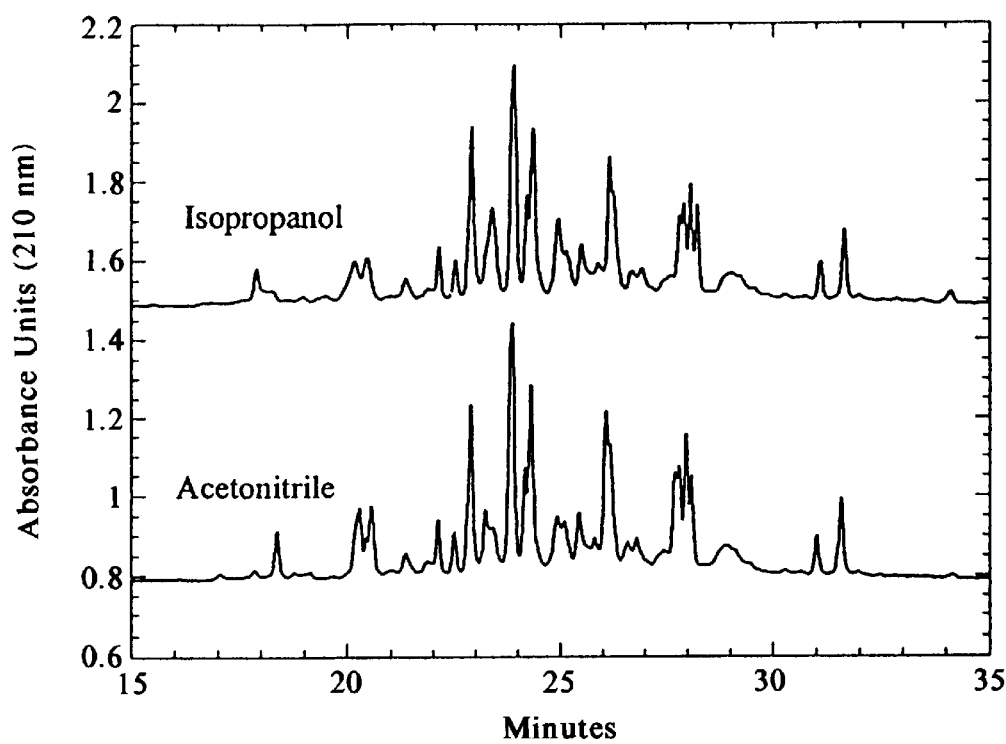
FIG. 2 shows the uv RP-HPLC trace obtained from a mixture of compounds added to a perfluorocarbon emulsion, comparing disruption of the emulsion using isopropanol or acetonitrile.

The first set of experiments was performed as described in Example 1, but acetonitrile was used in place of isopropanol. The plot in FIG. 2 shows a typical result in which recovery of the analytes was found to be identical when isopropanol was replaced with acetonitrile (HPLC grade; Fisher Scientific, Fairlawn N.J.) in the chemical disruption of the emulsion. This findings shows that acetonitrile can be used in place of isopropyl without compromising the recovery of the analytes in supernate derived from perfluorocarbon emulsions.

Figure 3:
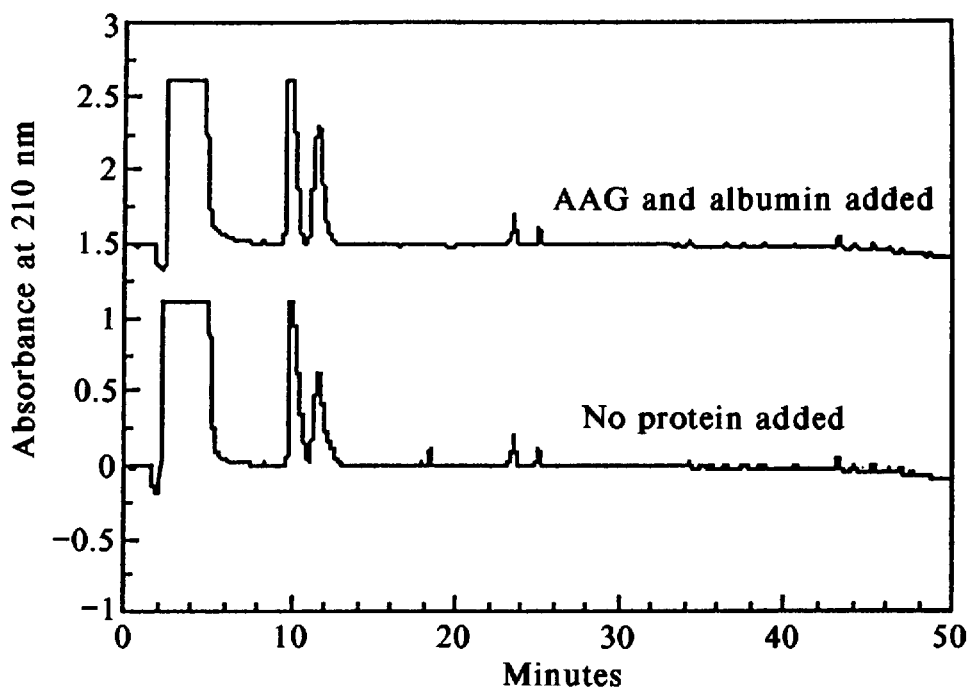
FIG. 3 shows the RP-HPLC trace obtained from a mixture of compounds added to a perfluorocarbon emulsion, obtained with and without added proteins.

(B) Protein Precipitation: In the second set of experiments, two of the most abundant proteins found in blood plasma were examined: albumin and alpha amino glycoprotein (AAG). Bovine serum albumin (minimum purity 99%; Sigma Chemical Co., St. Louis, Mo.) and alpha amino glycoprotein (AAG; minimum purity 99%; Sigma Chemical Co.) were added to OXYPHEROL-ET EMULSION™ (Alpha® Therapeutic Corp., Los Angeles, Calif.) at 4.5 and 0.8 mg/ml, respectively. As in part (A) above, acetonitrile was used to chemically disrupt the emulsion. The plot in FIG. 3 shows that the supernate derived from protein-amended emulsion had an HPLC profile that was indistinguishable from supernate from emulsion having no added proteins. This finding demonstrates that plasma proteins can be quickly and efficiently removed from perfluorocarbon emulsions using acetonitrile.

EXAMPLE 3

Perfusion of Rat GI Tract with Perfluorocarbon Emulsion

The objective of this experiment was to determine whether a perfluorocarbon emulsion is amenable to HPLC analysis after use in the blood vasculature of animals. An isolated portion of rat gastrointestinal tract was perfused by flushing with an emulsion and then perfusing the segment in a recirculating manner with emulsion, adding emulsion at the mesenteric artery, and extracting it at the portal vein.

To perform the experiment, we used a male, CD rat (Charles River, Wilmington, Mass.), weighing approximately 400 g. Following an overnight fast, the rat was anesthetized by administration of an intramuscular injection of ketamine and xylazine, and placed on a warming pad. Surgery was performed following a method described by Pang et al., *Drug Metab Disp* (1986) 14:102–11, incorporated herein by reference. Briefly, the abdomen was opened with a midline incision and the entire intestine was removed and placed on a saline-soaked gauze. The following clamps in the intestine and arterial and venous systems were made to isolate the blood vasculature of the intestine and prevent redirection of the perfusate through inosculated vessels: (1) the intestine (2 cm below the pylorus and immediately above the cecum); (2) the arterial system at the inferior mesenteric, gastric, splenic and hepatic arteries and the coeliac axis; (3) the venous system at the pyloric, pancreatico-duodenal and splenic veins; and (4) the aorta and vena cava above and below the superior mesenteric artery. The superior mesenteric artery was cannulated where it branches off the aorta and 1 ml of heparinized saline was injected. To flush the blood from the vasculature of the gastrointestinal tract, OXYPHEROL-ET EMULSION™ (Alpha® Therapeutic Corp., Los Angeles, Calif.) was perfused at a flow rate of 4 ml/min by means of an oscillating pump into the superior mesenteric artery while the portal outflow of blood was directed to a waste container. After a 10-min flush of the vasculature, the portal outflow of perfusate was directed back to a 100-ml reservoir of OXYPHEROL-ET EMULSION, thereby generating a closed loop in which the vasculature was perfused in a recirculating manner. The mesenteric system was then perfused for 45 min with 1 ml samples taken each 5 min from the 100-ml reservoir of OXYPHEROL-ET EMULSION. The samples were prepared for HPLC analysis as described in Example 1.

Figure 4:
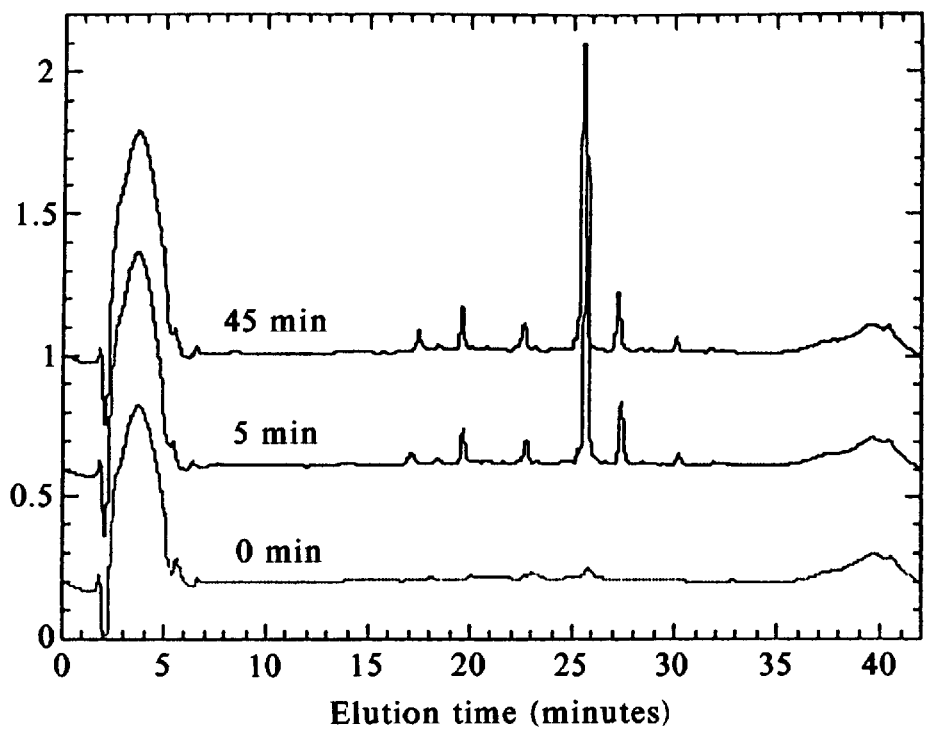
FIG. 4 shows the RP-HPLC trace obtained from perfusion of a perfluorocarbon emulsion through a portion of isolated rat gastrointestinal tract at 0, 5, and 45 minutes after beginning perfusion.

The plot in FIG. 4 shows that the "background" of the HPLC trace increases immediately (within 5 min) after perfusion through the gastrointestinal vasculature, and that this background remains constant over a 45 min observation period. These findings show that perfluorocarbon emulsions are amenable to HPLC analysis after use in the blood vasculature of animals.

What is claimed:

1. A method for determining pharmacokinetics of a test compound in an isolated live organ, comprising:
   (a) perfusing said isolated organ with a blood substitute, wherein said blood substitute is a fluorocarbon emulsion;
   (b) administering said test compound to said isolated organ;
   (c) removing a portion of said blood substitute from said isolated organ; (d) adding a water-miscible organic solvent to said portion to disrupt said emulsion; and
   (e) analyzing said portion for the presence of said test compound or its metabolites.

2. The method of claim 1, wherein said fluorocarbon emulsion is selected from the group of perfluorocarbons consisting of perfluorotributylamine, perfluorodecalin, perfluorooctyl bromide, perfluorotripropylamine, bis(perfluorobutyl)ethylene, perfluoro-N,N-dimethylcyclohexylmethylamine, perfluorotrimethylbicyclo(3.3.1)-nonane, perfluorobicyclo(5.3.0)decane, and perfluorobutyltetrahydrofuran.

3. The method of claim 2, wherein said fluorocarbon emulsion is perfluorotributylamine.

4. The method of claim 1, wherein said water-miscible organic solvent is selected from the group consisting of an alcohol, an amine, tetrahydrofuran, and pyridine.

5. The method of claim 1, wherein said water-miscible organic solvent is selected from the group consisting of isopropanol and acetonitrile.

6. The method of claim 1, wherein said test compound is administered as a mixture of test compounds.

* * * * *